United States Patent [19]
Salmasian

[11] 3,994,291
[45] Nov. 30, 1976

[54] SALMASIAN INFLATABLE INTRA-UTERINE DEVICE

[76] Inventor: Saeed Salmasian, Memorial Hospital, 119 Belmont St., Worcester, Mass. 01605

[22] Filed: July 1, 1974

[21] Appl. No.: 484,807

[52] U.S. Cl. ............................................. 128/130
[51] Int. Cl.² .......................................... A61F 5/46
[58] Field of Search ....................... 128/127–130, 128/341, 343, 344, 359, 1 R, 131, 246, DIG. 20, DIG. 25, 272, 260; 46/87–90

[56] References Cited
UNITED STATES PATENTS

| 525,785 | 9/1894 | Hurdle | 128/129 |
| 2,122,579 | 7/1938 | Meckstroth | 128/130 |
| 2,922,252 | 1/1960 | Van Dam et al. | 46/88 |
| 3,464,409 | 9/1969 | Murphy | 128/129 |
| 3,628,530 | 12/1971 | Schwartz | 128/130 |
| 3,693,266 | 9/1972 | Pressman | 46/87 X |
| 3,779,241 | 12/1973 | Vennard et al. | 128/129 |
| 3,811,423 | 5/1974 | Dickinson et al. | 128/343 |

FOREIGN PATENTS OR APPLICATIONS

| 818,086 | 10/1951 | Germany | 128/130 |
| 17,292 | 9/1894 | United Kingdom | 128/129 |

*Primary Examiner*—Lawrence W. Trapp
*Attorney, Agent, or Firm*—Buckles and Bramblett

[57] ABSTRACT

An intra-uterine device comprising a support member and a plurality of branch members connected to said support member and extending from all sides of said support member, said support member and branch members being inflatable and being adapted so as to fit substantially entirely within the uterine cavity of the user thereof.

31 Claims, 21 Drawing Figures

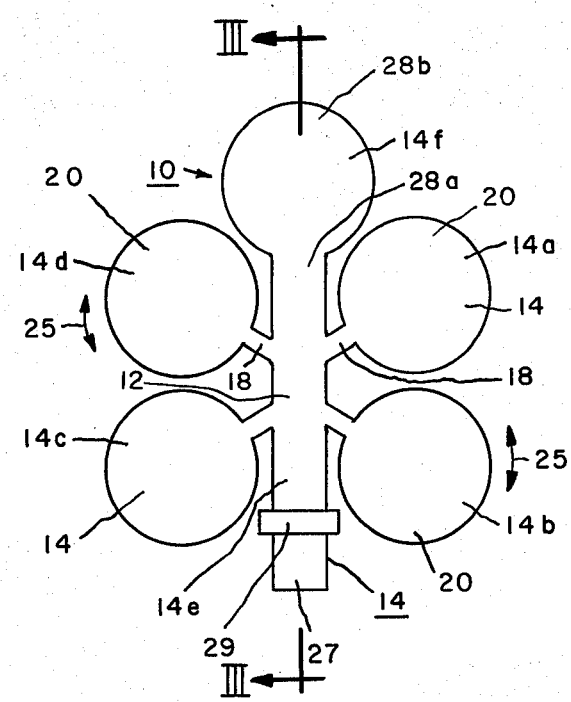
Fig. 1
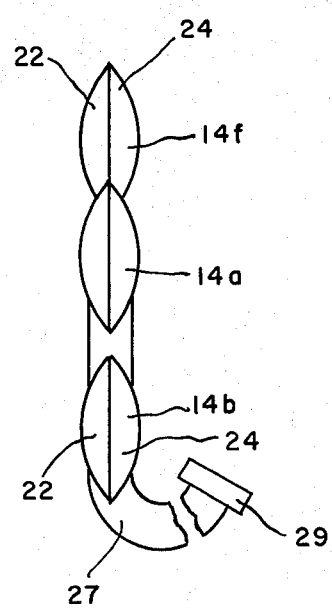
Fig. 2
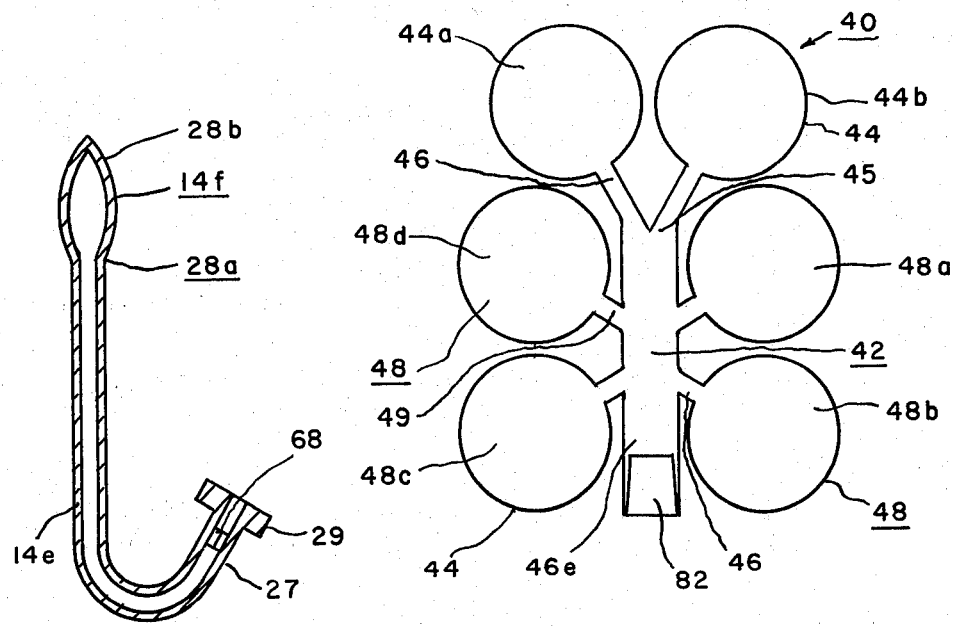
Fig. 3
Fig. 4

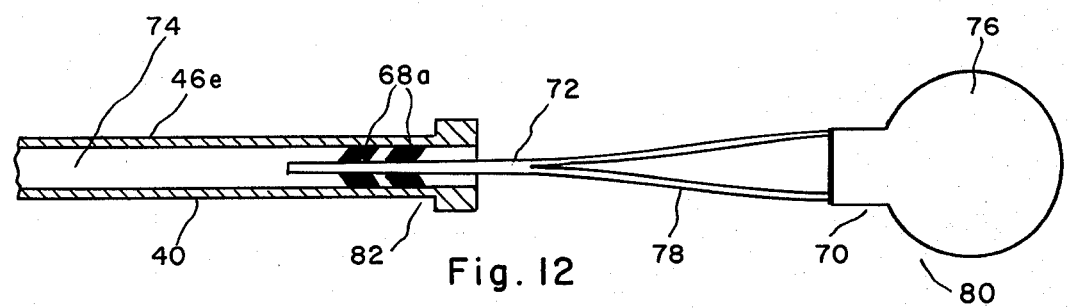
Fig. 12
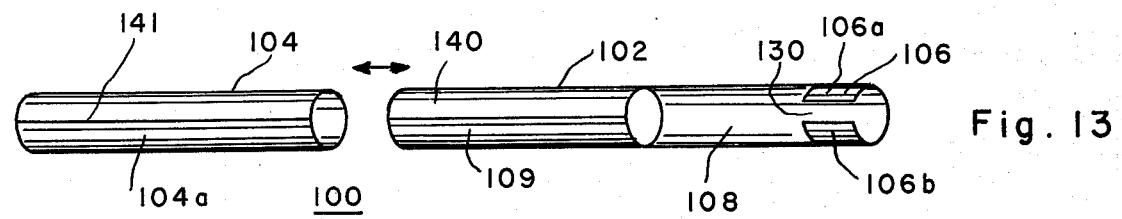
Fig. 13
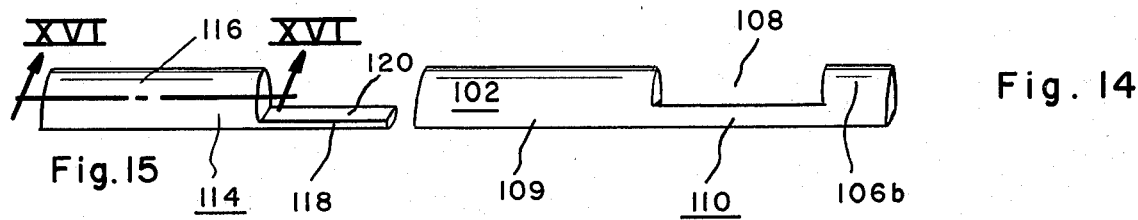
Fig. 14
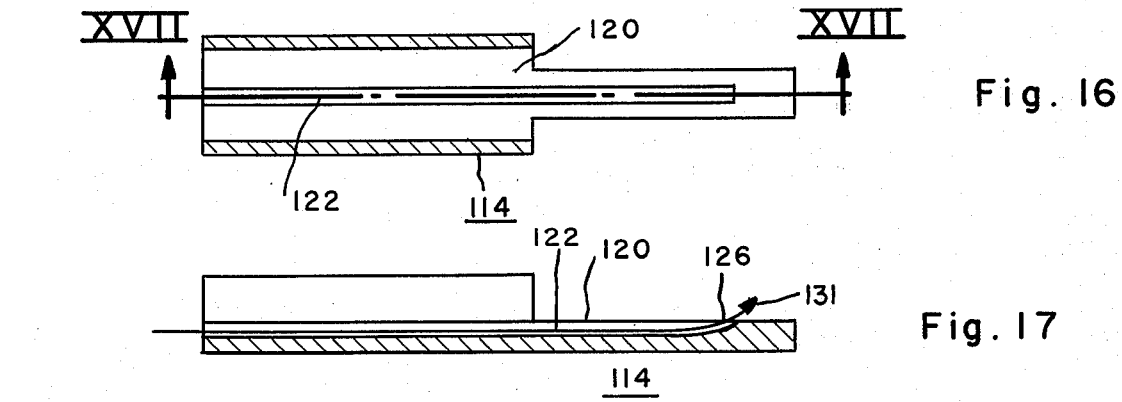
Fig. 16
Fig. 17

3,994,291

SALMASIAN INFLATABLE INTRA-UTERINE DEVICE

BACKGROUND OF THE INVENTION

The present invention relates to an intra-uterine device (I.U.D.), particularly to an inflatable such device for use as a contraceptive device.

Intra-uterine devices have come to be known and used generally and their mode of operation generally is well-known, at least to those practicing in the art, but many of the presently known varieties of intra-uterine devices suffer from a number of drawbacks and disadvantages, among the more prominent of which are the devices' increasing the susceptibility of the user to ascending uterine infection and/or bleeding; relatively facile expulsion of the device from the uterus of the user, relative difficulty and discomfort to the user in the insertion and removal of the device, etc.

For example, for type of I.U.D. is constructed as a solid body of flexible material, but this can cause discomfort to the user during insertion and/or removal of the device, for example. Other types of devices require the use of a strand or other filament that has one end connected to the I.U.D. with the other end thereof located in the vagina (when the device is located in the uterus), where it is accessible and can be used to remove the device from the patient's uterus. Such a strand is not desirable due to the high propensity for the patient to contract an infection of the uterus, which uterine infection can spread therefrom through the fallopian tubes to the ovaries. Such an infection is possible by reason of the fact that the strand or filament provides a path or route along which the germs, bacteria, etc., can move into the uterus, where they can cause an infection. Such a path or route is not present in the present invention.

Another I.U.D. in the prior art appears to be inflatable buy this device is of such shape as to contact a relatively small proportion of the uterine wall, and, as a further disadvantage, requires an extension thereof to extend through the cervical canal and into the vagina, thus leading to the significant possibility of uterine infection. Also, this device is more apt to be expelled from the uterus by uterine cotractions.

It is therefore, an object of the present invention to produce an intra-uterine device that overcomes, or at least alleviates to a significant extent, the foregoing shortcomings of various prior art devices and provides further benefits.

BRIEF SUMMARY OF THE INVENTION

The invention includes an intra-uterine device that comprises a support member and a plurality of branch members that are substantially co-planar with the support member and radiate in all directions (i.e., from all sides) from the support member, which support and branch members are inflatable with a fluid, and in which at least a major number of the branch members comprise a first portion connected to the support member and a second portion connected to the first portion but more remote from the support member than the first portion.

According to a preferred embodiment, the second portions comprise lateral regions extending beyond the lateral parts of their respective first portions, with a relatively abrupt transition region between the first and second portions.

BRIEF DESCRIPTION OF DRAWINGS

FIG. 1 is a front elevation view of the I.U.D. according to an embodiment of the invention.

FIG. 2 is a side elevation view of the device in FIG. 1.

FIG. 3 is a sectional side elevation view of the device in FIG. 1 along axis III—III.

FIG. 4 is a front elevation view of the present invention according to another embodiment.

FIG. 12 depicts the inflation of the present device shown in fragmentary, side elevation view.

FIG. 13 is a side isometric view of a device for removing the invention from the user.

FIG. 14 is a side elevation view of a first component part of the device in FIG. 13.

FIG. 15 is a perspective view of a second component part of the device in FIG. 13.

FIG. 16 is a directional top view of the second component in FIG. 15 along axis XVI—XVI.

FIG. 17 is a sectional side elevation view of the second component of FIG. 16 along axis XVII—XVII.

PREFERRED EMBODIMENT

Figure 5:
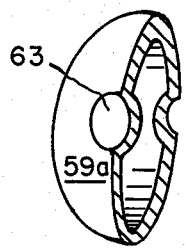
FIGS. 5, and 7 through 10 are sectional perspective views of the enlarged second portions of the invention according to further embodiments.

Referring to FIG. 1, the intra-uterine device (I.U.D.) 10, according to one embodiment of the invention has a shape resembling a star or a tree, wherein there is a support member 12 that preferably is centrally located and a plurality of branch members 14 that extend in different directions, and preferably, in all directions (i.e., from all sides) from the support member 12. The support and branch members 12, 14 are hollow and made of flexible or resilient material so as to be inflatable with a fluid, e.g., air or water. The branch members 14 and support member 12 preferably have substantially the same thickness (FIGS. 2 and 3) so that the device is of substantially uniform thickness.

At least a major number of branch members 14, preferably all of the branch members 14a through 14d that project laterally from the support member 12, individually comprise an interconnecting first portion 18 that is connected to the support member 12 and a larger second portion 20 located at the distal ends of the first portions 18 so as to be more remote from the support member 12. The second portions preferably are located close to each other so as to form a nearly continuous outline. Each second portion preferably has a circular (FIGS. 1 and 4, for example), ovate, or elliptical profile and comprises oppositely disposed surface members 22, 24 (FIGS. 2 and 3) that preferably are joined together in leak-proof fashion at their peripheries, the interiors of the branch and support members 14 and 12, respectively, preferably communicating with each other. The second portions, or nodules, 14 can be formed of an integral film or sheet material or, alternatively, can be formed of two sheets or films jointed together. The device itself can be formed from a single integral sheet or film or a plurality of such sheets joined together, e.g., two sheets having the outline shown in FIG. 1 and jointed at their peripheral parts.

The branch members 14 are able to pivot about their respective points of connection with the support member 12 (as indicated by arrows 25) so as to be conformable with the wearer of the device 10 and to yield and assume different orientations according to the movements of the wearer thereof.

The device 10 can include as one of the branch members 14 thereof a particular branch member 14e that is substantially an elongated body that preferably is of substantially uniform cross-section along substantially the entire length thereof, and, further, preferably has a distal portion 27 that forms in its natural condition a generally hook-shaped structure (FIG. 3) or a coiled structure or kink, for example, which distal portion 27 is extendible (as explained below) and is located entirely within the uterine cavity when the device 10 is in use, thereby avoiding the possibility of uterine infection, which is a severe drawback of prior art devices. It is preferred that the distal part of the branch member 14e include a lip or other enlarged portion 29 that forms a relatively sharp angle with the axis of the branch member 14e. The device 10 can include a branch member 14f that includes first and second portions 28a and 28b, respectively, that are axially aligned with the support member 12 and are connected at the end of the latter.

Figure 7:
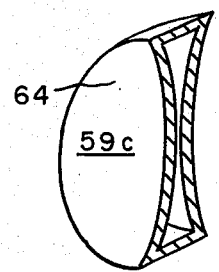

While the device 10 shown in FIG. 1, is particularly useful for nulliparous patients, the device 40 shown in FIG. 4 (which is similar in most respects to device 10) is useful for multiparous patients. The intra-uterine device 40 is an inflatable device that comprises a support member 42 that can be centrally disposed (as shown), and a plurality of branch members 44 that extend in all directions from the support member 42, with two branch members 44a and 44b disposed at the top end 45 of the support member 42 to form a generally Y-shaped or bifurcated structure there, with a major number of the branch members 44 individually comprising a first portion 46 connected to the support member 42 and a second portion 48 connected to the distal end 49 of the first portion 46. While the intra-uterine device of the present invention preferably is of substantially uniform thickness, a non-uniform thickness device is also satisfactory. The cross-sectional configuration of the second portions of the invention can be elliptical, double concave (FIG. 7), ovoid, double convex (FIG. 2), oblate, or other shape, to provide, e.g., a speroid or ellipsoid-shaped body. It is preferred that the general overall outline of the device (e.g., 10 in FIG. 1) be generally pearshaped to conform in shape with the uterine cavity the specific size of the device varying with the user. The support member 12 or 42 can be of elongated tubular shape and have a circular or other suitable configuration.

In both of the devices 10 (FIG. 1) and 40 (FIG. 4), it is preferred that the lower branch members (e.g., at least 14b and 14c of FIG. 1) thereof be angularly oriented with respect to the respective support members 12, 42 thereof and point downward (i.e., in retrograde) such that the respective second portions 20 and 44 thereof are below the ends of their respective first portions 18 and 46 that (i.e., the ends) are connected to the support members 12, 42. These lower branch members contact the lower extremities of the uterine cavity so as to serve as legs that support the decvice 10 or 40 that is disposed in the uterine cavity, with the elongated branch members thereof 14e and 46e located closest the cervical canal. The various other branch members closer to the top of the device 10 or 40, e.g., 14a and 14d of the device 10 of FIG. 1 or 48a and 48d of FIG. 4, can be disposed at acute, obtuse, and/or right angles with respect to the axis of the support member 12 or 42. It is preferred that the branch and support members of the devices (e.g., 10 and 40) of the invention be of such size and arrangement that a posterior or anterior view of such a device shows a relatively dense outline, i.e., there is relatively little open space between and among the branch and support members, so that there is a high degree of contact between the uterine cavity walls and the intra-uterine device (10, 40), e.g., greater endometrial surface contact, thereby providing greater contraceptive action. While the intra-uterine devices 10 and 40 as shown include, respectively, six and seven branch members 14 and 44, the numbers thereof can be otherwise, either more or less.

Figure 8:
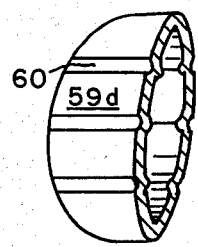
Figure 10:
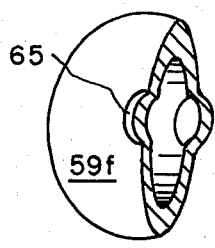
Figure 9:
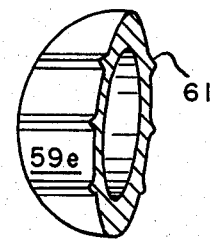
Figure 6:
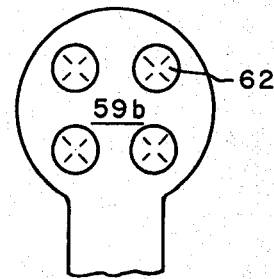
FIG. 6 is a fragmentary front fiew of a part of device according to the invention.

The various second portions, e.g., 20 and 48 in FIGS. 1 and 4, respectively, of the branch members can include surface members 22 and 24 in FIG. 2 (e.g., films that are joined together to form the pouch-like second portions), at least one (preferably both) of the surface members of one or more of the second portions (59a through 59f in FIGS. 5 through 10) of the branch members of a device e.g., 10 or 40, comprising discontinuities therein, e.g., grooves or ridges 60 (FIG. 8) or 61 (FIG. 9), localized depressions 62 at various locations at the central and/or peripheral areas (FIG. 6), a single depression 63 (FIG. 5) or depressions located at only the central region of the surface member or distributed along the periphery only or both, a concave or double concave 64 surfaces (FIG. 7), protruberances 65 that are located only at the central region (as shown in FIG. 6) or that are distributed over the surfce, or are located only at the peripheral parts, etc., which discontinuities increase or maximize the level of endometrial surface contact. The grooves 60 or ridges 61 can extend radially, parallel, or otherwise along the surface member.

While it is generally preferred that the first portions e.g., 18 in FIG. 1, of the branch members that are present on a device, e.g., 10, be of about the same length, first portions of different lengths (with the longer first portions located at the top, bottom or some intermediate point at the support member) can be used satisfactorily. Also, the lowermost branch members, e.g., 14b and 14c in FIG. 1, that project laterally from the support member 12 preferably form an acute angle with the axis of the support member 12, while the other branch members, e.g., 14a and 14d, projecting laterally from the support member 12 (or 42 in FIG. 4, where the lowermost branch members are numbered 48b and 48c and the upper members are numbered 48a and 48d) can form acute, obtuse, or right angles with the support member principal axis.

The intra-uterine device of the invention (e.g., 10 or 40) can be produced from any suitable material, such as, e.g., a flexible or pliable material, including rubber materials; natural and synthetic resins, which can include polyethylene, polypropylene, etc.; or others. The wall thickness of the device should be such as to withstand rupture when inflated and to contain in leak-proof fashion the fluid (water or gas) with which the intra-uterine device is filled.

Various means can be employed for containing the fluid within the intra-uterine device, one such way being, for example, one or more one-way valves 68, (which are commonly used for inflatable balls, such as footballs and basketballs), which valves 68 can be located in the elongated branch member 14e (FIG. 1) or 46e (FIG. 4). The valve or valves 68 preferably are located at the distal part of the branch member 14e or 46e, to make a substantial part of the branch member available for puncturing to deflate the device 10 or 40, as explained in detail hereinafter.

Figure 11:
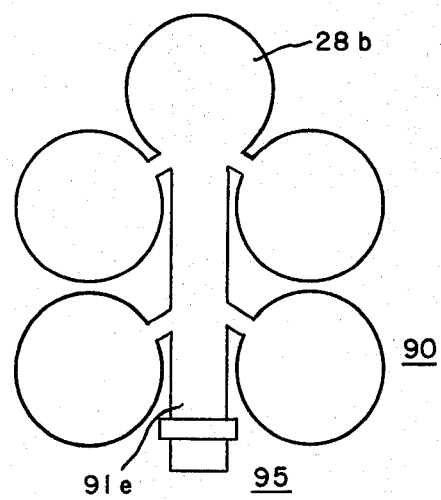
FIG. 11 is a front elevation view of the invention according to another embodiment.

To use the intra-uterine device (10, or 40, for example), a tubular insert instrument 70 (FIG. 12) is employed, which instrument 70 comprises a tubular elongated nose section 72 of relatively narrow size that can be inserted through the one or more valves 68a (FIG. 12) that are present in the elongated branch member, e.g., 46e of the device 40 (FIG. 4), so as to communicate with the interior 74 of the device 40. The instrument 70 can further comprise, for example, a plunger or piston mechanism (not shown) similar to that of a hypodermic needle or a deformable bulb 76 (as in a syringe, which the instrument 70 can be) as shown in FIG. 12, that is used to force the fluid contained in the instrument 70 into the intra-uterine device (e.g., 10, 40 or 90 in FIG. 11) until the device is inflated to the desired extent, generally to the fullest extent permitted by the size and shape of the uterine cavity. Where the inflating fluid is air or some other gas, the intra-uterine device can be inflated by connecting the insert element 78 containing the elongated nose section 72 to a source of compressed gas, as by rubber tubing, although alternative means for both liquid and gas inflating material can be used. To insert the intra-uterine device (10, or 40 90), the device is mounted on the insert instrument 70, as shown in FIG. 12, and the device is inserted head-first (i.e., the top part 14f in FIG. 1, etc, is inserted first) into the uterus, after which the insert instrument 70 is removed from the uterus (which is readily done since the inflated device will not be drawn out of the uterus due to the engagement of the uterine walls by the branch members) by pulling the insert instrument 70 out through the vagina. It is obvious that the length of the insert instrument should be such that the distal portions 80 remain outside the vagina to permit grasping the instrument 70 for removal and for depressing the plunger or deforming the bulb 76 in order to fill the device 40.

Upon the removal of the insert instrument 70 from the intra-uterine device 40, the distal portion 82 (FIG. 4) of the device 40 curls or becomes coiled, withdrawing completely into the uterus (if the device 40 is such that the length of the device is sufficiently long to permit it to be located in the cervical canal when the branch member 46e extended to a relatively linear condition, upon its curling the distal portion 82 withdraws completely therefrom) the distal portion in any event being located wholly within the uterus and not in the cervix, cervical canal, or vagina, thereby reducing significantly the possibility of a uterine infection, etc. The lower branch members (e.g., 48b and 48c in FIG. 4) bear against the lower parts of the uterine cavity effectively prohibiting the expulsion of the intra-uterine device through the cervical os.

For removing the device (10, 40 or 90, for example) from the uterine cavity, according to an embodimnet of the invention, removal apparatus 100 (FIG. 13) can be used, which removal apparatus comprises, preferably, first and second elements 102 and 104, one of which 102 is slidable within the other 104. The first element 102 can comprise a jaw portion 106 comprising a slotted tubular element, and an extension portion 108 connected at one end of the jaw portion 106, and, optionally, a tubular portion 109 that preferably is a slotted cylinder. The extension portion 108 preferably is more open with respect to the jaw portion 106 (i.e., the extension portion 108 has a lower side wall 110 (FIG. 14) that the jaw portion 106 so as to form a relatively shallow trought or is relatively planar with no significant side wall, so that the side wall of the extension portion 108, is, at most, smaller than the side walls 106a and 106b (FIG. 13) of the jaw portion 106. The second element 104 (FIG. 13) preferably comprises a slotted tubular, e.g., cylindrical or other configuration, part 104a and according to a preferred embodiment (FIG. 15, where parts corresponding to the structure in FIG. 13 are similarly numbered) the second element 114 comprises such a slotted cylindrical or tubular part 116 and also an extended trough section 118 (FIG. 15), which trough section 118 can have relatively shallow side walls or can be substantially flat (the latter being shown). It is preferred that the second element 104 or, as shown in FIG. 16, 114 also include at the interior surface 120 (FIG. 16) thereof a groove or channel 122 for receiving a rod member 130 (e.g., a needle having sufficient length as described below) that is used for puncturing and deflating the device 10, 40 or 90 which groove includes an inclined portion 126 (FIG. 17) at the end thereof. It is preferred that the cylindrical portion 109 of the first element 102 be located at the end of the extension portion more removed from the jaw portion 106, which cylindrical portion 109 can be slidably disposed within the second element 104 during use, it being preferred that the transverse exterior dimension of the cylindrical portion 109 be slightly less than the transverse interior dimension of the second element 104, such that there is a slight engagement therebetween that prevents the movement of one relative to the other without the application of external force.

The first and second elements 102 and 104 can be made of a synthetic resin such as polyethylene, Teflon (trademark of E.I. DuPont), or other suitable (e.g., flexible or pliable) material, Teflon or similar materials being preferred because of their natural lubricity. It is preferred that the first and second elements be dimensioned so that the first element is always during use partialy located within the second element. e.g., the cylindrical portion 109 of the first element 102 is at least substantially equal in length to the slotted cylindrical part 104a or 116 of the second element 104 or 114.

The slot 130 (FIG. 13) of the jaw portion 106 preferably is sufficiently wide to permit the elongated branch or tail, (e.g., 14e, 46e, or 91e of FIGS. 1, 4 and 11), of the device (10, 40, or 95, respectively, the I.U.D. 95 being similar to the other devices 10, 40 in most respects) but not the flared or lip portion (e.g., 29 of FIG. 1) where one is present, to pass therethrough, as explained below. The slots 141 and 140, respectively, in the cylindrical part 104a of the second element 104 and in the cylindrical portion 109 of the first element 102 provide resilience or springiness thereto, thus facilitating the motion of the former through the latter. While the jaw portion 106, cylindrical portion 109 and cylindrical part 104a are described as having substantially circular cross-sections, other configurations may be used.

Figure 18:
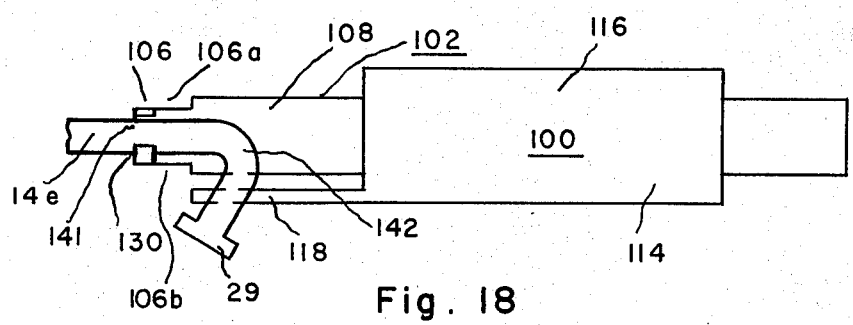
FIG. 18 is a side elevation view of an I.U.D. removal device and a fragmentary part of the device being removed from the I.U.D. user.

In removing the intra-uterine device 10, 40, or 90 (FIGS. 1, 4 and 11, respectively) from the uterine cavity, the removal apparatus 100, which is arranged so that the jaw portion 106 is located within the cylindrical part 104a or 114 (FIGS. 13 and 15, respectively) or, where there is one present, at the trough section 118 so that their ends are substantially aligned (with the slot of the jaw portion 106 turned down to be adjacent to trough section 120) to provide a continuous circumferential surface (to avoid the presence of corners that are not desirable since the end of the removal device 100 at which the jaw portion 106 is located generally is the leading edge and is inserted first into the vagina and uterus) and the apparatus 100 is inserted into the patient so that the end of the apparatus 100 at which the jaw portion 106 is located, is in the uterus and the opposite end is outside the patient. The first element 102 (FIG. 18) is then rotated within the second element 104 so as to expose the slot 130 of the jaw portion 106 and the first element 102 is advanced beyond the extension portion 118 of the second element 114 so that the jaw portion 106 is located beyond the second element. The uncurled part 141 i.e., the part between the kink or bend, 42 and the support member 112 in FIG. 1, for example, of the elongated branch member (e.g., 14e in FIG. 1) is then introduced into the interior of the jaw portion 106 via the slot 130 and the first element 102 is rotated to bring a wall member 106a or 106b of the jaw portion 106 to a position where it can engage the curled part or bend 142 of the elongated branch member 142, after which the first element jaw portion 106 is moved toward the second element 114, which results in the jaw portion 106 straightening the curled part 142. The first element 102 is then rotated so that the extension portion 108 is disposed above the groove or slot 122 (FIGS. 16 and 17) to restrict the movement of the branch member and then the rod 131 (FIG. 17) is moved along the groove or slot 122 to the inclined groove portion 126 by which it is directed toward the elongated branch member 14e. The rod is forced into the elongated branch member 14e to puncture the latter and thereby permit the inflating fluid to be drained from the device 10 (or 40 or 90) and deflate the device 10.

Figure 19:
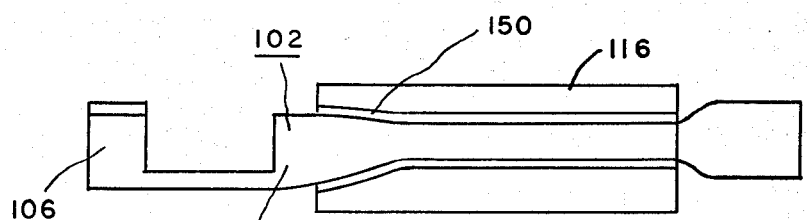
FIG. 19 is a side elevation view of the removal device of FIG. 18.

To remove the device (10, for example), from the patient, the removal apparatus 100 is withdrawn from the uterus and out of the vagina, the wall portions 106a and 106b engaging the enlarged or lip portion 29 so that the device 10 is removed with the apparatus 100. Alternatively, the end of the rod 131 can be barbed to hold the device while it is extracted or other means for holding can be used, e.g., the inner transverse dimension of the second element cylindrical part 116 (FIG. 19) can be tapered down (over at least part of the length of the cylindrical part 116) in the direction toward the end of the second element 114 located outside the patient to provide a tapered section 150 (FIG. 19) that urges the wall members 106a and 106b of the jaw portion 106 toward the elongated branch member 14e so as to engage and hold the latter during withdrawal of the device (the first and second elements 102 and 114 being removed together).

It can be seen that, contrary to prior art devices, the present invention does not utilize, require, or include a strand, filament, or other part located outside the uterus when the present intra-uterine device is in use. Also, in contrast to the prior art, the present invention is inserted head (i.e., upper part) first into the uterus and removed therefrom tail (i.e., lower part) first, thus avoiding the need to invert or turn the device (e.g., to turn the device 180° so that the head portion is at the cervical canal) and avoiding this procedure which can be uncomfortable to the user.

It can also be seen that, because the first (i.e., the extended) portions of the various branch members are internally hollow, they are more flexible so as to pivot more freely and with greater ease about the support member than a branch that is solid, so that the present invention is more comfortable for the user or patient. In addition to water and air, other fluids, i.e., gas or liquid, can be used for inflating the present I.U.D., which I.U.D. is not of a pre-set unalterable size and configuration, but instead can conform to a greater degree with the shape and size of the uterus since it is inflated in situ.

According to another embodiment of the invention, the I.U.D. inserting device 160 (FIG. 20) can comprise a structure that includes two channels 162 and 164 (e.g., two attached tubular members or an integral structure comprising two channel portions), a first one of the channel 162 providing a path for introducing the inflating fluid into the intra-uterine device 166 which has its elongated branch member (or stem) 168 conneted to the end of the structural part 170 defining the channel 162. The second channel 164 contains an elongated holding device 180 that includes a bifurcated part 182 at one end, the prongs of the part 182 being urged together when the part 182 is located in the channel 164 but springing apart (at least the bifurcated part 182 being made of springy or resilient material such as rubber, plastic or metal, for example) when they are moved beyond the edge of the structural part 172 defining the second channel 164 within which the holding device 180 is slidably disposed. The device 160 preferably includes also a spacing element 190 that serves to limit the motion of the device 160 into the uterus, the element 190 preferably being located (e.g., about 4 cm, from the end of the structural part 170) so as to engage the cervix but not pass into the cervical canal, in which way the I.U.D. 166 can be inserted in the uterus with only a small part, if any, of the structural parts 170, 172 entering into the uterus. In this way, damage by the device 160 to the uterus (e.g., perforation of the uterus, etc.) can be avoided.

To use the device 160, the elongated branch member 168 (comparable to 14e in FIG. 1) of the I.U.D. 166 mounted in leakproof manner on the structural part 170 for supplying fluid, with the I.U.D. held between the prongs 184, 186 that are disposed within the channel or conduit 164 so as to firmly grasp the I.U.D. 166. The holding device 180 is then slid out of the channel 164, thereby permitting the prongs 184, 186 to separate freeing the device 166. The fluid then is passed into the I.U.D. 166 until inflation has reached the desired level after which the inserting device 160 is separated from the inflated I.U.D. and removed from the user.

Figure 20:
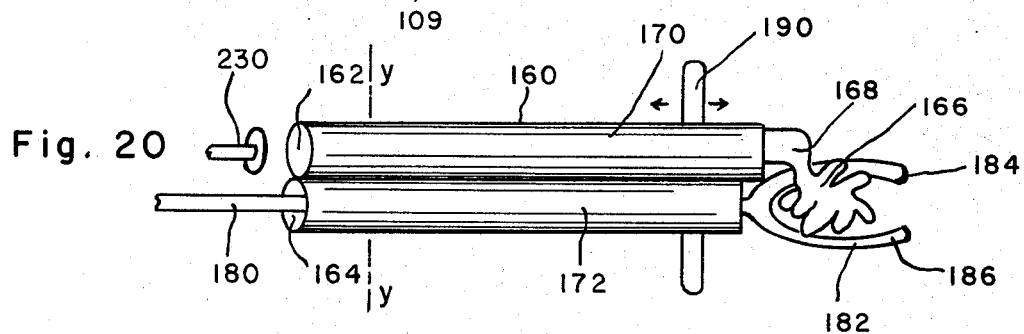
FIG. 20 is a side elevation view of an apparatus according to the invention, for inserting the device of the invention.

The spacing element 190 can be an annular ring connected to the structures 170, 172, a plurality of projecting spikes extending in different directions (as shown in FIG. 20) or otherwise.

Figure 21:
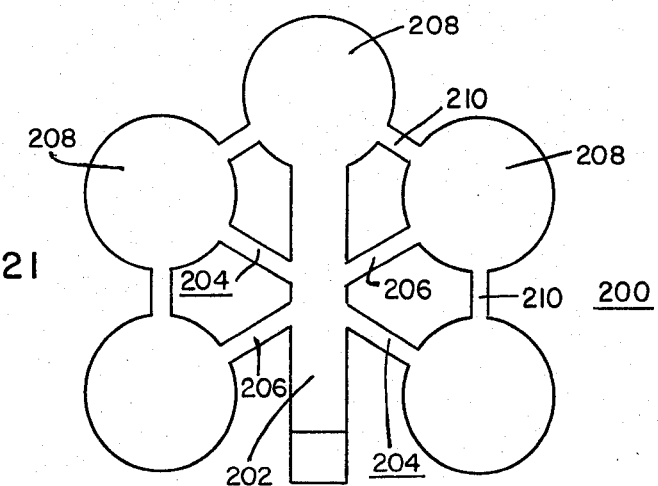
FIG. 21 is an elevational view of another embodiment of the present invention.

According to a still further embodiment, the present invention can comprise an inflatable intra-uterine device 200 (FIG. 21) can have a structure similar to those previously described (i.e., with a hollow support member 202 and a plurality of hollow branch members 204 extending in different directions therefrom, most of the branch members individually comprising an interconnecting first portion 206 and an enlarged or bulbous, second portion 208 with a relatively abrupt transition therebetween), except that the device 200 further comprises an extension element 210 that is located and extends between the respective ones of a pair of branch members 204, it being preferred that there be at least one such extension element 210 between respective branch members 204 of at least a major number of the pairs of such branch members.

It is especially preferred that the extension elements also be hollow and that their respective interiors cooperate with their associated branch members 204 so as to be inflatable therewith. It is also more preferred that the extension elements be located between the second portions 208 of their associated branch members 204 so as to form a peripheral frame (FIG. 21) over at least a major part of the device circumference.

Referring back to FIG. 20, the spacing element 190 can be mounted so its position on the structure 170, 172 can be adjusted, the spacing element being temporarily fixed at a particular station on the structure for a certain patient and subsequently moved for another patient, thereby permitting the degree of insertion of the inserting device 160 into the patient to be adjusted according to the patient's physcial structure and dimensions. Where it is desired, a single mechanism can simultaneously operate the holding device 180 (i.e., it can move the holding device 180 out of the channel 164) and feed the inflating fluid into the I.U.D. through a syringe element, for example, located at the end of the channel 162 for conducting the inflating fluid through the valves of the device. According to a preferred mode of inflating the Salmasian I.U.D., the I.U.D. is inflated by the fluid to a maximum size (that can be determined by the size of the uterine cavity), after which back-pressure builds up to the point where the syringe is expelled from the I.U.D., after which the inserting device is removed.

Where it is desired, a spacing element (e.g., one comparable to spacing element 190 in FIG. 20) can be included in any of the other embodiments of the present invention.

The fluid may be introduced into the device 166 (FIG. 20) via a plunger mechanism 230 that can enter and slide along the opening 162 so as to force the fluid into the device 166.

I claim:

1. An intra-uterine device comprising a support member having plural sides and a plurality of branch member connected to said support member and extending from all said sides of said support member, said support member and branch members being inflatable and being adapted so as to fit substantially entirely within the uterine cavity of the user thereof, wherein at least a major number of said branch members individually comprise first portions of elongated shape and second portions, said second portions being more remote from said support member than their respective said first portions and being connected to said support member by said first portions, said second portions comprising respective lateral regions extending beyond the lateral parts of said first portions and there being a relatively abrupt transition between said first and second portions.

2. An intra-uterine device as in claim 1, wherein said second portions are disposed proximate to each other so as to form a generally continuous loop comprising said second portions.

3. An intra-uterine device as in claim 1, wherein a said branch member consists entirely of an elongated first branch member disposed at a first side of said support member, said first branch member being of substantially uniform cross-section.

4. An intra-uterine device as in claim 3, wherein a single said branch member is disposed at an opposite second side of said support member.

5. An intra-uterine device as in claim 4, wherein said single branch member and said support member are substantially co-axial.

6. An intra-uterine device as in claim 3, wherein a bifurcate pair of said branch members are disposed at a second side of said support member and individually are obliquely disposed with respect to the axis of said support member.

7. An intra-uterine device as in claim 6, wherein said branch members individually form an acute angle with the axis of said support member.

8. An intra-uterine device as in claim 1, wherein said second portions individually comprise first and second oppositely disposed major surface members.

9. An intra-uterine device as in claim 8, wherein at least one of said surface members of said device comprises a discontinuity.

10. An intra-uterine device as in claim 8, wherein at least one of said major surface members comprises at least one depressed region.

11. An intra-uterine device as in claim 10, wherein said depressed region comprises a generally grove shaped structure.

12. An intra-uterine device as in claim 10, wherein said depressed region comprises a generally pocket shaped structure.

13. An intra-uterine device as in claim 10, wherein said depressed region comprises a generally channel shaped structure.

14. An intra-uterine device as in claim 8, wherein at least one of said major surface members of said device comprises at least one protrusion.

15. An intra-uterine device as in claim 8, wherein at least one of said surface members of said device comprises a concave area.

16. An intra-uterine device as in claim 8, wherein said surface members are joined together at their respective peripheral portions.

17. An intra-uterine device as in claim 2, wherein said first portions are individually relatively flexible.

18. An intra-uterine device comprising a support member having plural sides and a plurality of branch members connected to said support member and extending from all of said sides of said support member, said support member and branch members being inflatable and being adapted so as to fit substantially entirely within the uterine cavity of the user thereof, wherein one of said branch members is elongated and disposed at a side of said support member, the respective interiors of said elongated branch member and said support member communicate with each other and said elongated branch member includes at least one fluid valve.

19. An intra-uterine device as in claim 18, wherein said elongated branch member comprises an area of weakness that is adapted to be ruptured, thereby permitting the fluid contents of said device to be removed.

20. An intra-uterine device as in claim 18, wherein said branch member comprises a terminal portion remote from said support member, said terminal portion forming an extendible curled portion that is entirely disposed within the uterine cavity of the user.

21. An intra-uterine device comprising a support member having plural sides and a plurality of branch members connected to said support member and extending from all of said sides of said support member, said support member and branch member being inflatable and being adapted so as to fit substantially entirely within the uterine cavity of the user thereof, wherein at least all of said branch members projecting laterally from said support member individually comprise both a tubular first portion connected at one end thereof to said support member and an enlarged second portion at the other end of said first portion, the respective interiors of said support member and said first and second portions communicating with each other.

22. An intra-uterine device comprising a support member having plural sides and a plurality of branch members connected to said support member and extending from all of said sides of said support member, said support member and branch members being inflatable and being adapted so as to fit substantially entirely within the uterine cavity of the user thereof, wherein said branch members comprise inflatable enlarged distal portions, at least one of said enlarged portions having a profile configuration that is circular, ovate, or elliptical.

23. An intra-uterine device comprising a support member having plural sides and a plurality of branch members connected to said support member and extending from all of said sides of said support member, said support member and branch members being inflatable and being adapted so as to fit substantially entirely within the uterine cavity of the user thereof, wherein a particular said branch member consists of tubular structure characterized by a plastic memory, such that said tubular structure can coil upon itself, said tubular structure comprising an enlarged distal portion.

24. An intra-uterine device as in claim 23, wherein said enlarged portion forms a relatively sharp angle with the axis of said tubular structure.

25. An intra-uterine device comprising a support member having plural sides and a plurality of branch members connected to said support member and extending from all of said sides of said support member, said support member and branch members being inflatable and being adapted so as to fit substantially entirely within the uterine cavity of the user thereof, wherein a particular said branch member is axially aligned with said support member and is connected to the end thereof, said particular branch member having its interior in communication with said support member and comprising an elongated first portion connected at one end thereof to said support member and an enlarged second portion remote from said support member and connected to the opposite end of said first portion.

26. An intra-uterine device comprising a support member having plural sides and a plurality of branch members connected to said support member and extending from all of said sides of said support member, said support member and branch members being inflatable and being adapted so as to fit substantially entirely within the uterine cavity of the user thereof, wherein at least one of said branch members comprises an elongated first portion connected to said support member and an enlarged second portion connected to the distal end of said first portion, the cross-sectional configuration of said second portion being elliptical, double concave, ovoid, double convex, concavo-convex, double convex, or oblate.

27. An intra-uterine device comprising a support member having plural sides and a plurality of branch members connected to said support member and extending from all of said sides of said support member, said support member and branch members being inflatable and being adapted so as to fit substantially entirely within the uterine cavity of the user thereof, wherein lower ones of said branch members are oriented in a retrograde direction.

28. An intra-uterine device as in claim 27, wherein said lower branch members comprise tubular first portions and enlarged second portions at least partly disposed below said first portion.

29. An intra-uterine device as in claim 27, wherein upper ones of said branch members are oriented with respect to said support member so as to form individually therewith an angle that is acute, obtuse, or right angle.

30. An intra-uterine device comprising a support member having plural sides and a plurality of branch members connected to said support member and extending from all of said sides of said support member, said support member and branch members being inflatable and being adapted so as to fit substantially entirely within the uterine cavity of the user thereof, wherein plural said branch members comprise substantially tubular first portions and second portions, at least one of said second portions individually comprising at least one surface discontinuity, thereon, said discontinuity being located at at least one of the interior and peripheral surface parts of said second portion.

31. An intra-uterine device as in claim 30, comprising plural said discontinuities distributed over the surface of said second portion.

* * * * *

UNITED STATES PATENT OFFICE
CERTIFICATE OF CORRECTION

Patent No. 3,994,291          Dated November 30, 1976

Inventor(s) SAEED SALMASIAN

It is certified that error appears in the above-identified patent and that said Letters Patent are hereby corrected as shown below:

Cancel "Salmasian" from title. Col. 1, line 20, change "for" (second occurrence) to --one--; line 39, change "buy" to --but-- line 45, change "cotractions" to --contractions--. Col. 2, line 13, change "fiew" to --view--; line 25, change "directional" to --sectional--. Col. 3, line 56, change "speroid" to --spheroid--; line 59, insert a comma (,) between "cavity" and "the". Col. 4, line 5, change "decvice" to --device--; line 16, delete "a device" and insert therefor -- such devices-- line 42, change "6" to --10--. Col. 6, line 2, change "embodimnet" to --embodiment--; line 14, change "that" to --than--; line 15, change "trought" to --trough--; line 54, change "partialy" to --partially--. Col. 7, lines 29, 30, 31, delete "i.e., the part between the kink or bend, 42 and the support member 112 in FIG. 1, for example". Col. 8, line 56, before "mounted" insert --is--. Col. 10, line 40, change "grove" to --groove--.

Signed and Sealed this

Twenty-fourth Day of May 1977

[SEAL]

Attest:

RUTH C. MASON
Attesting Officer

C. MARSHALL DANN
Commissioner of Patents and Trademarks